United States Patent
Bixler et al.

(10) Patent No.: US 7,333,002 B2
(45) Date of Patent: Feb. 19, 2008

(54) AUTOMATICALLY TRACKING MOBILIZED EQUIPMENT AND NURSE CALL PRIORITY ASSIGNMENT SYSTEM AND METHOD

(75) Inventors: Craig Bixler, Saint Charles, IL (US); Scott Hutchinson, South Elgin, IL (US); Brent Bergwall, Carpentersville, IL (US)

(73) Assignee: GE Security, Inc., Bradenton, FL (US)

( * ) Notice: Subject to any disclaimer, the term of this patent is extended or adjusted under 35 U.S.C. 154(b) by 252 days.

(21) Appl. No.: 11/138,457

(22) Filed: May 27, 2005

(65) Prior Publication Data
US 2006/0267740 A1    Nov. 30, 2006

(51) Int. Cl.
*G08B 5/00* (2006.01)

(52) U.S. Cl. .............. 340/286.07; 340/5.91; 340/10.1; 340/10.42; 340/286.01; 340/539.13; 340/825.49; 705/2; 705/28

(58) Field of Classification Search ........... 340/286.07, 340/286.01, 310.01, 310.03, 310.06, 538, 340/10.1, 572.1, 539.13, 10.42, 825.36, 825.49, 340/539.12, 5.91, 5.92, 310.11; 705/1, 2, 705/28; 238/385
See application file for complete search history.

(56) References Cited

U.S. PATENT DOCUMENTS

| | | | | |
|---|---|---|---|---|
| 5,732,401 A * | 3/1998 | Conway | ...................... | 705/29 |
| 5,910,776 A * | 6/1999 | Black | ........................ | 340/10.1 |
| 6,943,683 B2* | 9/2005 | Perret | ......................... | 340/538 |
| 6,989,749 B2* | 1/2006 | Mohr | ....................... | 340/572.1 |
| 6,998,978 B2* | 2/2006 | Kirkeby | ................. | 340/539.12 |
| 7,123,149 B2* | 10/2006 | Nowak et al. | ........... | 340/572.1 |

* cited by examiner

*Primary Examiner*—Davetta W. Goins
(74) *Attorney, Agent, or Firm*—Baker & Hostetler LLP

(57) ABSTRACT

By combining the information acquired from a location system that is tracking equipment and/or personnel within a hospital environment, automatic assignment of the "relocated" patient monitoring equipment can be made in concert with a nurse call system. By utilizing time-based elimination criteria, monitoring equipment that is coupled to generic port can be automatically processed for port priorities, and equipment assignment changes. An event subscription manager with location bridges and nurse call bridges facilitate the automatic association of the patient monitoring equipment to the respective nurse call system and intended information therein. By use of the automatic association paradigms, manual alarm and assignment tasks can be minimized.

19 Claims, 1 Drawing Sheet

AUTOMATICALLY TRACKING MOBILIZED EQUIPMENT AND NURSE CALL PRIORITY ASSIGNMENT SYSTEM AND METHOD

FIELD OF THE INVENTION

The present invention relates generally to patient monitoring equipment and nurse call systems. More particularly, the present invention relates to systems and methods for automatically assigning priority to patient monitoring equipment when being integrated into a nurse call system by use of location tracking and time-basing the equipment's proximity.

BACKGROUND OF THE INVENTION

Hospitals use a variety of patient monitoring equipment to alert them of potential patient needs. Virtually all monitoring devices act in a stand-alone fashion, providing an audible alarm when an alert condition occurs. Many devices also provide a relay closure output to signal, or interface to nurse call systems. This allows the monitor alarm to appear at the door light, at the nurse console, on pagers and phones, and in nursing unit activity and response time reports. These alerts, however, are generic in nature and do not typically specify the type of alarm at hand. This is because the overhead and risk of mistake in manually updating the alarm priority outweigh the benefits of a unique alarm. Ideally, the nurse call alarm display from patient monitoring equipment would be unique to the specific type of monitoring device connected: i.e. IV drip, ventilator, or heart monitor.

Accordingly, it is desirable to provide systems and methods that overcome many of these deficiencies and provide the ability to automatically assign patient monitoring equipment on a "location-based" paradigm, rather than physical assignments from manual configuration.

SUMMARY OF THE INVENTION

The foregoing needs are met, to a great extent, wherein a embodiments in accordance with the present invention provides systems and methods which uses the intelligent assignment of priority to a patient monitoring port using wireless equipment location information.

In accordance with one embodiment of the present invention, An automatic equipment assignment system is provided, comprising a wireless tracking system data communication interface, a nurse call system data communication interface, and an event subscription system coupled to the wireless tracking system data communication interface and the nurse call system data communication interface, wherein the event subscription system assigns mobilized equipment that has been wirelessly tracked and coupled to an equipment communication port, to a nurse call system coupled to the nurse call system data communication interface.

In accordance with another embodiment of the present invention, a method of automatically assigning equipment to a nurse call system is provided, comprising the steps of communicating location information of a wirelessly tracked mobilized equipment, assigning a priority of the mobilized equipment based on the location information, and communicating the assigned priority to a nurse call system.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
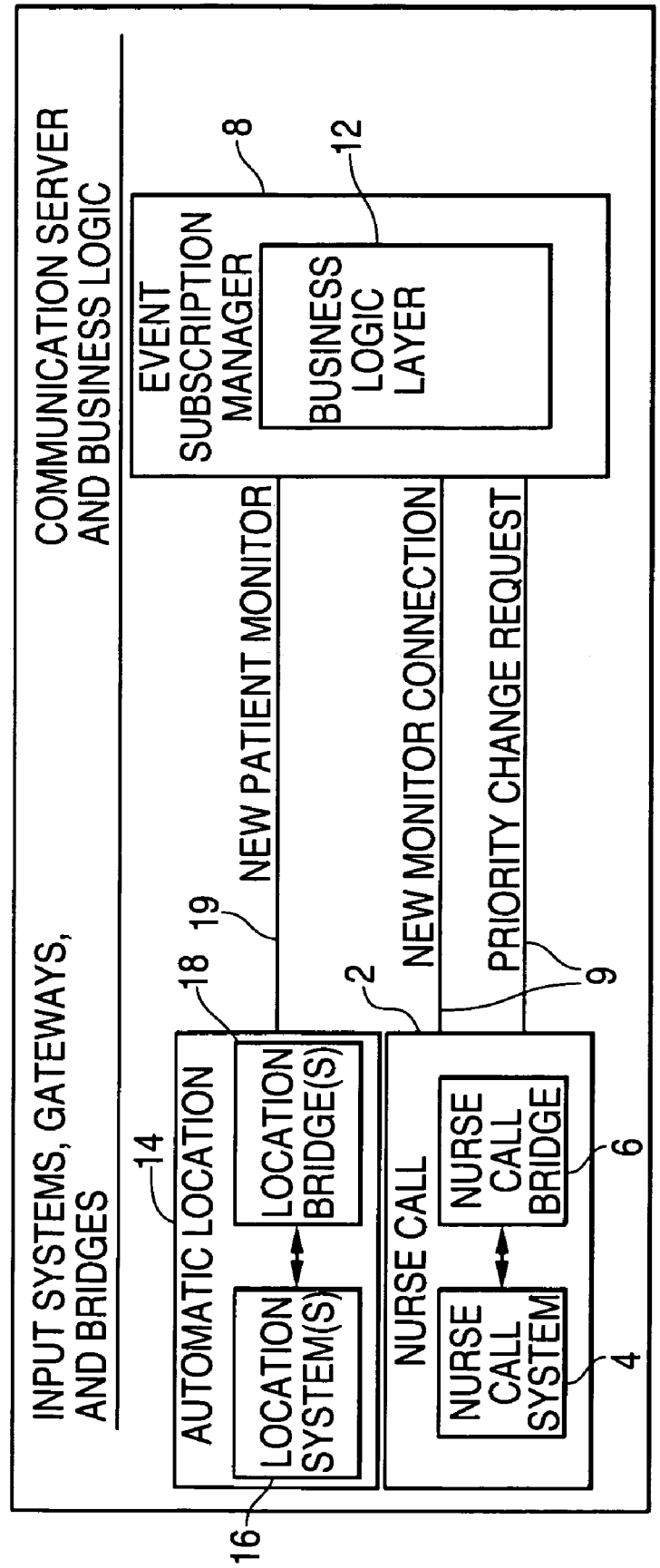
FIG. 1 is a block diagram illustrating a sequence of events and flow of information in an exemplary embodiment of the invention.

The invention will now be described with reference to the drawing figures, in which like reference numerals refer to like parts throughout.

In an automatic location system, an ID badge is attached to a person or piece of equipment, and transmits a wireless signal (infrared, ultrasonic, RF, or a combination). Processing software receives these signals, attaches room names and staff or equipment names and types to the ID's, and sends staff and equipment movement and status messages to clients via an application programming interface (API).

Badges and transmissions generally take one of two forms. In the first form, badges are transmitters only, which frequently transmit only their unique ID. Frequency rates are typically ever 2 seconds to every minute, depending on the expected rate of movement of the staff or equipment the badge is attached to, and on the sleep state of the badge, which may be, light or motion sensor controlled. The transmission range is typically short (inherent in IR and ultrasonic technology, and accomplished in RF technology by attenuating the RF signal to minimize the range) and picked up by a local receiver that can pinpoint the location of the badge, and then transmit its location ID and the badge ID to the location system processing software. (RF triangulation has also been attempted with varying degrees of success.)

In the second form, the badges are transceivers. They will receive a short range IR, RF, or ultrasonic location specific beacon signal from a room transmitter. Based on the signal, the badge can determine if it has changed locations, and if so, can issue a long-range transmission (typically RF) that includes the badge ID, the new location ID, and perhaps the old location ID. Long-range receivers then forward this signal to the system processing software. Badges will also typically send an occasional supervisory signal (every minute to 30 minutes) to inform the system of their current location, and that they are still alive.

By combining the events from the location system and the nurse call system, an intelligent assignment of priority to a patient monitoring port can be made with a high degree of confidence in the reliability of that assignment. The location system can indicate the arrival of a new piece of patient monitoring equipment into a room. If the location badge type corresponded to a priority within the nurse call, that badge would indicate a piece of monitoring equipment whose alarm should be assigned its unique priority. The nurse call system can indicate the connection of a piece of monitoring equipment into the port of that same room. If the two events happen within a reasonable time frame of each other (several minutes) and if only one piece of equipment is in the room and not assigned to a port, that piece of equipment can be inferred as being connected to the port, and the port could be assigned a priority specific to that piece of equipment. Accordingly, automatic priority and/or port assignment can be accommodated through an intelligent "fusion" of the badge location and a nurse call system port registration information.

In addition, client software can log the assignment changes, could provide a warning of unassigned equipment in the room, of unassigned port priorities, and can automatically reassign ports to a generic priority when equipment leaves the room or when port/equipment ambiguity is detected.

Based on the above exemplary methods, FIG. 1 is a block diagram 10 illustrating an exemplary sequence of the event or information pathways. The exemplary diagram 10 contains a nurse call component 2 containing a nurse call system 4 with a nurse call bridge 6. The nurse call bridge 6 is in communication with the nurse call system 4 and with an events subscription manager 8. The event subscription manager 8 contains a business logic layer 12. Communication between the nurse call component 2 and the event subscription manager 8 is facilitated through communication channels 9. Communication channels 9 enable new monitor connection and priority change requests to be exchanged between the various systems.

An automatic location component 14 is also in communication with the event subscription manager 8. The automatic location component 14 contains a location system 16. The location system 16 is coupled to a location bridge 18. The location bridge 18 enables communication between the location system 16 and the event subscription manager 8 via communication channel 19. New patient monitor indication and assessment information is communicated to the event subscription manager 8. The event subscription manager 8 contains a business logic layer 12 which is updated and tabulated with information arriving from the automatic location component 14 and the nurse call component 2.

In operation, as a new patient monitor arrives within a room having a designated patient therein, location sensing equipment using radio frequency, ultrasonic, infrared, acoustic, etc., methods or systems can be used to log the arrival of the new patient monitor within the room. Such systems can be any one of the systems described herein, such as an RFID system or the like. Of course, alternative non-RFID systems having similar equivalent functionalities may be used according to design preference. With a logging of the new patient monitor in the automatic location component 14, the event subscription manager 8 is notified and assignments can be designated in the event subscription software relating to the room name, staff, equipment types, ID's, messages, programming, alert status, etc., relating to the newly arrived patient monitor. Based on the hierarchy of priorities and assignments programmed into the event subscription manger 8, the business logic layer 12 can respond to alerts, updates, equipment movement, staff assignments, etc. that may have a bearing on the nurse call system 2. Other possible examples, though not limited herein, may include priority changes conflicts with equipment or staff, inventorying, and other desired functions. The business logic layer 12 can comprise software components or software processes coupled to databases, as needed. Alternatively, tables having information regarding the associations between patient monitor equipment and nurse call alerts that assignments can be implemented according to design preference.

The nurse call component 2 or features or elements therein, such as the nurse call system 4, may be portable which may be moved between the rooms or floors of a building. Thus, the nurse call component 2 may similarly have a location update feature relevant to the event subscription manager 8. Alternatively, the nurse call component 2 may have specific features that are tailored for a particular patient monitor equipment and based on such correlations, the event subscription manager 8 may activate or deactivate these features upon the monitor connection. Conversely, certain nurse call components 2 and patient monitors may have non-compliant capabilities wherein the event subscription manager 8 and the business logic layer 12 may include programming such as translators or emulators to facilitate a conversion of the non-compliant capabilities to enable at least some form of connection of the patient monitor and nurse call system 4, whether to enable generic or specific functions.

As described above, the location system 16 may comprise of any one or more of commonly known or future derived location systems, for example, RFID, ultrasonic, infrared, light, etc. Such systems may be distributed having central transmitters/transceivers/detectors or may be of a hub-spoke arrangement. Accordingly, various alterative arrangements may be utilized without departing from the spirit and scope of this invention. For example, in the exemplary embodiment 10, the locator bridge 18 may be a RFID transceiver or location detector within the sensing environments. The acquired location and identity of the equipment, personnel, patient, etc, is obtained by the automatic location component 14, which may be an independent, stand-alone system. Information from the automatic location component 14 may be forwarded to the event subscription manager 8 via wireless or wired communication (e.g., communication channel 19). Assuring the automatic location component's 14 location information is compatible with the format of the event subscriptions manager 8, the event subscription manager 8 processes the location (and equipment identity/type) and associates this patient monitoring equipment to a priority relating to a designated or appropriate nurse call system 4 or nurse call component 2.

If independent location system(s) 16 and/or the nurse call system(s) 4 have non-compatible data or communication formats with respect to the event subscription manager 8, the location bridge(s) 18 and/or the nurse call bridge(s) 6 may operate as a translating mechanism to facilitate compatibility between the various systems. Accordingly, disparate pre-existing systems may be retro-fitted with location bridge(s) 18 and/or nurse call bridge(s) 6, operating under an automatic location component 14 and/or nurse call component 2, respectively, to accommodate implementation of the exemplary invention.

It should be appreciated that the various systems and components described herein may be implemented in software or hardware, or a combination thereof. Therefore, the various systems and components may be implemented in a computer such as a personal computer, server, networked controller, microcontrollers, etc. Various systems and components and methods described here may also be readily implemented in software using interpreted or executable code which may be used on a variety of computer or work station hardware platforms. Whether software or hardware is used to implement the various systems and components herein is dependent on the speed and efficiency requirements of the system, the particular functions, and the particular software or hardware systems and microprocessor or microcomputer systems being utilized.

If a software implementation is utilized, the program may be an embedded code, for example, Assembler, interpreted code, Basic, C, etc. Of course, other programming languages such as object-oriented languages, for example, may be used without departing from the sprit and scope of this invention. Thus, one of ordinary skill having read the disclosure here and may contemplate numerous other variations made feasible by the state of the art. For example, asynchronous computing, parallel, peer-to-peer computing, socket-based, distributed, master-slave, impeded, scaleable system, etc., may be used. Additionally, multitasking or separate modules in the form of subroutine calls implemented as a single multi-capable process utilizing fork or child processes to enable multi-thread operations may be implemented.

It should be appreciated that while FIG. 1 illustrates a single automatic location component 14 and a single nurse call component 2, multiple components may be contemplated without departing from the sprit and scope of this invention. Similarly, the event subscription manager 8 is illustrated as a single unit. Based on the hardware and software implementation paradigm chosen, the event subscription manager 8 may be a multi-distributive process operating on several computing platforms or a single process operating on an individual platform.

By utilizing the exemplary method and system described in FIG. 1, conventional location systems which have only been contemplated in the prior art in the context of inventory control, can now be exploited to include room/patient assignment, staff assignments, alert and alarm management, etc. With the use of such an exemplary system 10, in a hospital environment, for example, patient monitoring equipment which enters a patient's room can be plugged into a generic port or into a network without the requirement of manual tracking of the equipment. By enabling the automatic location and tracking of patient monitoring equipment, the event subscription manager 8 may access the generic port or network to query or program the new patient monitor. By determining the time-based location of the patient monitor, the event subscription manger 8 can determine that the signal arriving from the generic port or network is due to the time-correlated patient monitor's integration into the system.

Conversely, an un-plugging scenario may similarly be determined by the event subscription manager 8 when a "disconnect" signal is received from the generic port or network for a patient monitoring system that has recently been indicated by the automatic location component 14 as having left location with the "disconnect" signal. By incorporating the time-based location of various patient monitoring equipment, specific "manual" updating or connection of the patient monitoring equipment to a dedicated or specialized connection can be obviated. Furthermore, manual updating of the priority or other desired information of a nurse call system 4 can be obviated by the automatic operation of the events subscriber manager 8.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An automatic equipment assignment system, comprising:
   a wireless tracking system data communication interface;
   a nurse call system data communication interface; and
   an event subscription system coupled to the wireless tracking system data communication interface and the nurse call system data communication interface, wherein the event subscription system assigns mobilized equipment that has been wirelessly tracked and coupled to an equipment communication port, to a nurse call system coupled to the nurse call system data communication interface, wherein the event subscription system assigns a priority of the mobilized equipment to the nurse call system.

2. The automatic equipment assignment system of claim 1, wherein the wireless tracking system data communication interface translates non-event subscription system readable information to an event subscription system readable format.

3. The automatic equipment assignment system of claim 2, wherein the translation is performed by an event subscription translator.

4. The automatic equipment assignment system of claim 1, wherein the nurse call system data communication interface translates non-event subscription system readable information to an event subscription system readable format.

5. The automatic equipment assignment system of claim 4, wherein the translation is performed by an event subscription translator.

6. The automatic equipment assignment system of claim 1, wherein the event subscription system maintains a database of assignments.

7. The automatic equipment assignment system of claim 1, wherein event subscription system determines the assignment based on a room-derived location and a time of the location of the mobilized equipment.

8. The automatic equipment assignment system of claim 1, wherein the event subscription system determines assignments for a plurality of mobilized equipment.

9. The automatic equipment assignment system of claim 1, wherein the event subscription system determines assignments for a plurality of nurse call systems coupled to the nurse call system data communication interface.

10. The automatic equipment assignment system of claim 1, further comprising:
    a wireless tracking system coupled to the wireless tracking system communication interface.

11. The automatic equipment assignment system of claim 10, wherein the wireless tracking system is RFID-based.

12. A method of automatically assigning equipment to a nurse call system, comprising the steps of:
    communicating location information of a wirelessly tracked mobilized equipment;
    assigning a priority of the mobilized equipment based on the location information; and
    communicating the assigned priority to a nurse call system.

13. The method of automatically assigning equipment to a nurse call system, of claim 12, further comprising the step of:
- at least translating the wirelessly tracked mobilized equipment communication to a computer readable format to enable computerized assignment and translating the assignment to a nurse call system readable format.

14. The method of automatically assigning equipment to a nurse call system of claim 12, wherein the assignment is based on a room-derived location and a time of the location of the mobilized equipment.

15. The method of automatically assigning equipment to a nurse call system of claim 12, wherein the assignment is based on information retrieved from a database.

16. The method of automatically assigning equipment to a nurse call system of claim 12, wherein alert information and status of the mobilized equipment is configured based on the assigned priority.

17. The method of automatically assigning equipment to a nurse call system of claim 12, where in the computerized assignment is performed by an event subscription system.

18. The method of automatically assigning equipment to a nurse call system of claim 17, wherein assignments are dynamically updated based on a most current identified location of the mobilized equipment.

19. The method of automatically assigning equipment to a nurse call system of claim 12, wherein priority assignments are first requested to an event subscription system, prior to an actual assignment of priority.

* * * * *